United States Patent
Bernhardt

(10) Patent No.: US 9,358,026 B2
(45) Date of Patent: Jun. 7, 2016

(54) GRIPPING INSTRUMENT

(71) Applicant: OLYMPUS WINTER & IBE GMBH, Hamburg (DE)

(72) Inventor: Dennis Bernhardt, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 14/407,711

(22) PCT Filed: Jun. 20, 2013

(86) PCT No.: PCT/EP2013/062918
§ 371 (c)(1),
(2) Date: Dec. 12, 2014

(87) PCT Pub. No.: WO2014/001200
PCT Pub. Date: Jan. 3, 2014

(65) Prior Publication Data
US 2015/0164526 A1    Jun. 18, 2015

(30) Foreign Application Priority Data
Jun. 25, 2012    (DE) .......... 10 2012 210 763

(51) Int. Cl.
*A61B 17/00* (2006.01)
*A61B 17/29* (2006.01)
(Continued)

(52) U.S. Cl.
CPC ............. *A61B 17/29* (2013.01); *A61B 17/2812* (2013.01); *A61B 17/2841* (2013.01);
(Continued)

(58) Field of Classification Search
CPC ............... A61B 17/28; A61B 17/2841; A61B 17/0483; A61B 17/44; A61B 2017/2905; A61B 17/29; A61B 17/2812; B25G 1/02

USPC ......... 606/139, 144, 147, 205, 206, 207, 208; 81/342, 417
See application file for complete search history.

(56) References Cited

U.S. PATENT DOCUMENTS 3,325,897 A    6/1967    Luebkeman
3,636,954 A *  1/1972    Weston .......................... 606/208
(Continued)

FOREIGN PATENT DOCUMENTS

| DE | 8810869 U1 | 10/1988 |
|---|---|---|
| DE | 9213119 U1 | 11/1992 |
| DE | 102006042985 A1 | 4/2007 |
| EP | 0450608 A1 | 10/1991 |
| JP | H08-38492 A | 2/1996 |

OTHER PUBLICATIONS

Oct. 1, 2013 International Search Report issued in Application No. PCT/EP2013/062918.
(Continued)

*Primary Examiner* — Tuan V Nguyen
(74) *Attorney, Agent, or Firm* — Oliff PLC

(57) ABSTRACT

A gripping instrument with two jaw parts, which are connected to each other by a pivot joint and are movable toward each other, by pushing together of two grip arms connected to the jaw parts, and are movable away from each other, by pushing apart of the grip arms, wherein the grip arm has a bending joint, by means of which, when the grip arms are pushed together, a force limited by a resiliency of the bending joint is transmitted, via the grip arm with the bending joint, to the corresponding jaw part, and which bending joint includes a directional abutment, wherein an applied manual force acts directly through the directional abutment during the pushing apart.

16 Claims, 3 Drawing Sheets

(51) Int. Cl.
- *B26B 13/12* (2006.01)
- *A61B 17/28* (2006.01)
- *B25J 1/04* (2006.01)
- *A61B 17/32* (2006.01)
- *A61B 17/12* (2006.01)

(52) U.S. Cl.
CPC *B25J 1/04* (2013.01); *B26B 13/12* (2013.01); *A61B 2017/12004* (2013.01); *A61B 2017/2905* (2013.01); *A61B 2017/2908* (2013.01); *A61B 2017/320044* (2013.01)

(56) References Cited

U.S. PATENT DOCUMENTS

| | | | |
|---|---|---|---|
| 7,234,377 B2 * | 6/2007 | Wolfson | B25B 7/02 81/415 |
| 2008/0215048 A1 * | 9/2008 | Hafner et al. | 606/42 |

OTHER PUBLICATIONS

Oct. 1, 2013 Written Opinion issued in Application No. PCT/EP2013/062918.

* cited by examiner

GRIPPING INSTRUMENT

The invention relates to a gripping instrument, in particular a surgical gripping instrument, with two jaw parts, which are connected to each other by a pivot joint and are movable toward each other, by pushing together of two grip arms connected to the jaw parts, and are movable away from each other, by pushing apart of the grip arms. The jaw parts are arranged in the distal direction from the joint, and the grip parts, designed as handles, are arranged in the proximal direction from the joint.

Forceps-like surgical instruments of this kind are well known and, in the simplest case, can be chosen such that one of two jaw parts and one of two associated handles are in each case formed integrally, and the resulting two pieces are connected crosswise to each other, like scissors, by means of a pivot joint.

In addition to simple gripping instruments of this kind, complex gripping instruments are also known, for example for laparoscopic use, in which a manual force applied to the handles is guided, for example via a linkage, to the jaw parts connected to each other in the manner of a hinge. An example of such an instrument is described in EP 0 450 608. In the instrument described there, a handle acts on a pulling and pushing rod via a bending joint in order to move a movable jaw part.

A manual instrument is likewise known from DE 88 10 869 U1, in which a maximum force to be applied to jaws of the instrument is limited by a bending location in one of the handles.

The object of the present invention is to make available a simple gripping instrument that is easy to use.

According to the invention, this object is achieved by a gripping instrument of the type mentioned at the outset, in which the grip arm has a bending joint which provides much greater yield when the grip arms are pushed together than when the grip arms are pushed apart, thus resulting in a directional abutment that is active during the pushing apart. In this way, during the pushing apart of the grip arms, an applied manual force acts at least more or less directly, i.e. the manual force is not limited by the resiliency of the bending joint provided for force limitation, whereas, when the grip arms are pushed together, a force limited by a bending of the bending joint is transmitted to the corresponding jaw part via the grip arm with the bending joint.

The gripping instrument according to the invention has the advantage that it is easy to use but at the same time of a particularly simple construction. Thus, the gripping instrument according to the invention is suitable for gripping even very fine tissue structures with a limited force. When the grip arms are moved toward each other, the bending joint formed by the grip arm experiences a bending action and thus limits a force acting on the corresponding jaw part and therefore on biological tissue located between the jaw parts. In turn, a pushing apart of the grip arms causes a moving apart of the jaw parts, with practically no reduction in manual force, which is useful, for example, for dissection of tissue. By virtue of the fact that the bending joint has a directional abutment that is active when the grip arms are pushed apart, i.e. during a movement that is performed typically in dissection of tissue, a practically unlimited manual force can be applied to the jaw parts, via the grip arm with the bending joint, and, finally, to the tissue to be dissected.

The grip arm can have a bending joint formed integrally with the grip arm, such that the gripping instrument is of particularly simple construction.

In the present case, a bending joint formed integrally with the grip arm is understood as a resilient bending joint in the sense of a compliant mechanism which is formed by a portion of the grip arm that is relatively flexible in one direction.

In a particularly preferred embodiment, the bending joint is formed by a cross-sectional tapering of the grip arm. A cross-sectional tapering of the grip arm can be formed by means of one or more slits made on one side on the grip arm. The remnant of the grip arm, left by the cross-sectional tapering of the grip arm and lying in the plane of the slits, defines a base web of the bending joint. The base web is thus left as a remainder by a cross-sectional tapering of the grip arm. In the simplest case, the bending joint function can thus be achieved by slits in the grip arm. The flexibility of the bending joint is defined by the geometrical moment of inertia of the base web. This is less than the geometrical moment of inertia at a location on the grip arm where no slit is provided. The mutually opposite end faces of the flanks of a respective slit can form the directional abutment of the bending joint that is active when the grip arms are pushed apart. The grip arm is preferably slit on one side. A slit can start from a side of the grip arm facing away from the respective other grip arm. This results in particularly directionally stable maneuverability of the gripping instrument.

It has proven advantageous if the grip arm has a plurality of slits along its longitudinal direction. A respective slit can, for example, be formed by slits oriented transversely with respect to the longitudinal direction of the grip arm. By suitable arrangement of the slits along the grip arm, it is possible to obtain at least an approximation to a uniform, orbit-like closing movement when two grip arms are pushed together.

The spacing between two adjacent slits can in each case define a comb web of the bending joint. A comb web can extend from the side of the grip arm, from which the slit issues, to the base web of the grip arm.

In a particularly preferred embodiment aimed at further improving the ergonomics of a closing curve defined when two grip arms are pressed together, the slits and/or the comb webs can have different widths. Likewise, the slits and/or the comb webs can be spaced apart from each other at different distances. The slits can also have different depths. Depending on requirements, a gripping instrument can, for example, be adapted to the individual needs of an operator or to the demands of a biological tissue. A width of a slit or of a comb web is understood as an extent of the slit or the comb web oriented in the longitudinal direction of the grip arm. A depth of a slit means an extent of the slit oriented transversely with respect to the longitudinal direction of the grip arm and lying in the pivot plane of the grip arms.

It has proven advantageous if the gripping instrument has a spring element arranged along the base web. The spring element is preferably embedded in the respective grip arm of the grip instrument, in particular completely embedded therein.

If the slits are especially wide, it has proven particularly advantageous if the comb web has a support element protruding from it, which support element is designed to brace the comb web against a respectively adjacent comb web when the grip arms are moved away from each other. By means of the support element protruding from the comb web, a directional abutment that is active during the pushing apart of the grip arms can also be achieved in the case of wider slits.

Moreover, in order to meet greater demands in respect of hygiene, the slit can be filled with a comparatively soft elastic filler component. Alternatively or in addition, a tapering of the slits can be enclosed by a sleeve separate from the grip arm. The flexibility of the sleeve can be made such that the sleeve does not tear when the grip arms are pushed together.

It is thus possible to avoid, for example, bacterial colonization in the slit, but also damage to biological tissue, e.g. by pinching, for example in a narrow opening of the body. The filler component can, for example, be a soft elastic plastic, e.g. a two-component injection mold, but also another filler material that is able to support the desired bending properties of the bending joint.

For particularly cost-effective production, the gripping instrument itself is preferably manufactured from an injection-molded plastic, for example. The jaw part and the associated grip arm can be formed integrally. A spring element of the bending joint can be made available as a steel spring but also as a plastic with a desired bend characteristic.

In another preferred embodiment, the gripping instrument has a rotation abutment which limits a movement of the jaw parts toward each other. The rotation abutment can be formed in direct proximity to the pivot joint on the grip arm and/or on the jaw part.

In order to avoid a plastic deformation and/or a fracture of a grip arm during the pushing together of the grip arms, the grip arm can have a safety abutment. The safety abutment limits a pushing together of the two grip arms in such a way that the grip arm and/or a bending joint formed on the grip arm are deformed only elastically. The safety abutment is preferably arranged proximally on the grip arm.

The gripping instrument is preferably a surgical gripping instrument. The gripping instrument can also be in particular an electrosurgical gripping instrument. For this purpose, suitable electrodes for cutting and/or coagulating biological tissue can be arranged on the jaw parts.

The invention will now be explained in more detail on the basis of an illustrative exemplary embodiment and with reference to the figures, in which.

Figure 1:
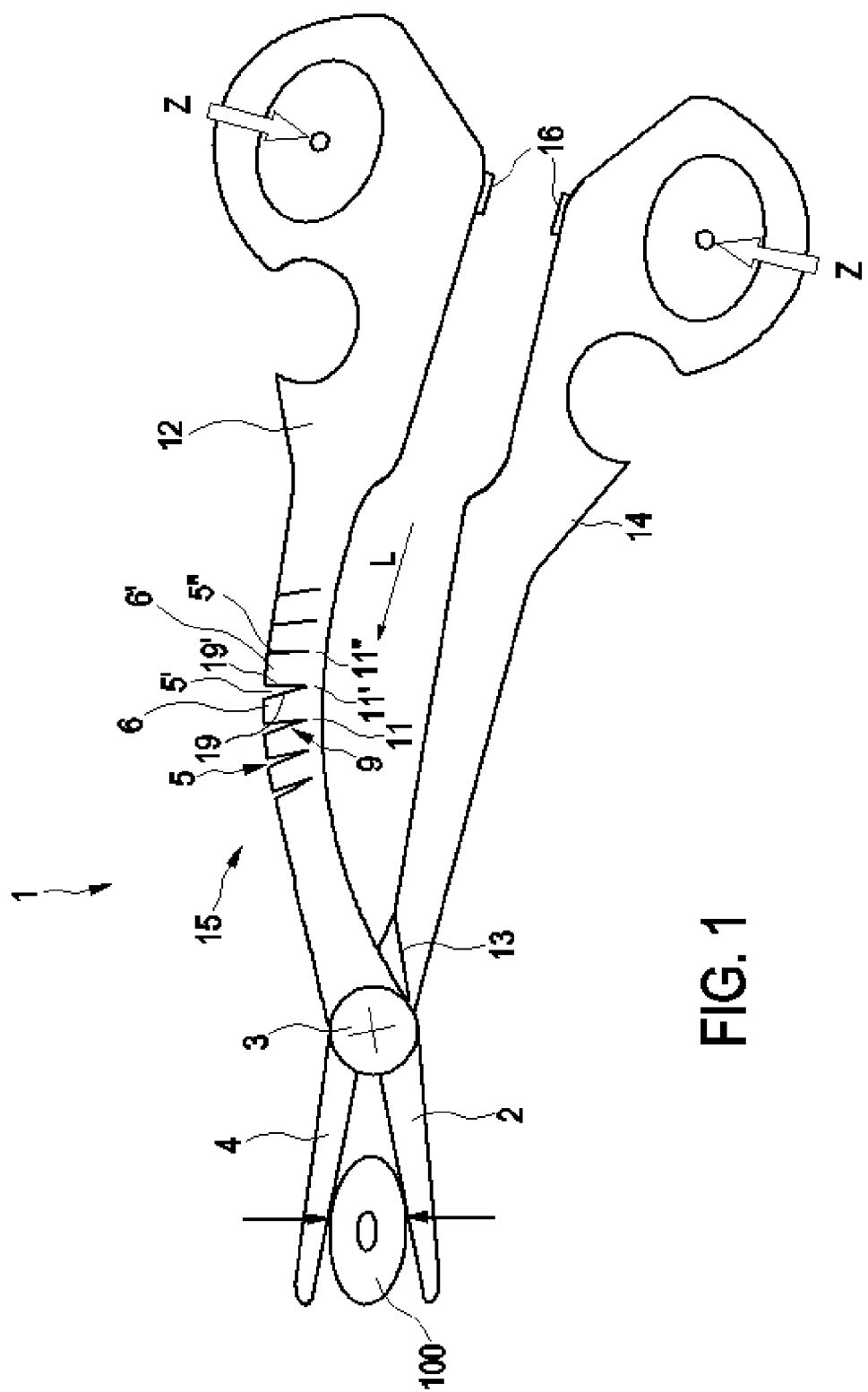
FIG. 1 shows a gripping instrument according to the invention during the pushing together of the grip parts.

A gripping instrument in FIG. 1 has a first jaw part 2 and a second jaw part 4. The first jaw part 2 and the second jaw part 4 are connected to each other by a pivot joint 3. A first grip arm 12, assigned to the first jaw part 2, is connected to the first jaw part 2, and a second grip arm 14, assigned to the second jaw part 4, is connected to the second jaw part 4. By pushing the grip arms 12 and 14 together, as is indicated by the arrow direction Z, the jaw parts 2 and 4 are also moved toward each other. The gripping instrument 1 is shown here gripping biological tissue 100. The grip arm 12 has a bending joint 15, which is formed on the first grip arm 12 and integral with the first grip arm 12. The bending joint 15 is formed by a cross-sectional tapering of the first grip arm 12, by means of several slits 5, 5', 5" arranged on one side on the first grip arm 12. The slits 5, 5' and 5" are in this case formed in the first grip arm 12, obliquely with respect to the longitudinal direction L of the first grip arm 12. The slits 5, 5' and 5" start from the side of the first grip arm 12 facing away from the second grip arm 14. It can be seen clearly in FIG. 1 that the slits 5, 5' and 5" are spaced uniformly apart from one another along the longitudinal direction L of the first grip arm 12. A uniform spacing relates here to a bending joint in the unloaded state (see FIG. 2).

As a result of the cross-sectional tapering of the first grip arm 12 by means of the slits 5, 5' and 5", a base web 11, 11', 11", starting from the foot of the slits 5, 5' and 5", is left as a remnant of the grip arm 12. A base web 11, 11', 11" is therefore a portion of the grip arm 12 reduced by a respective slit 5, 5' and 5". The base webs 11, 11', 11" extend, like the slits 5, 5' and 5", obliquely with respect to the longitudinal direction L of the first grip arm 12. The flexibility of the bending joint 15 is defined now by the geometrical moment of inertia of these base webs 11, 11', 11", wherein the geometrical moment of inertia of the base webs 11, 11', 11" is less than the geometrical moment of inertia at a location on the grip arm where no slit is provided.

It will also be seen from FIG. 1 that a comb web 6, 6' is formed in each case between two directly consecutive slits 5, 5', 5". The comb webs 6, 6' are therefore the portions of the first grip arm 12 which, in the longitudinal direction L of the first grip arm 12, lie between two directly consecutive slits 5, 5', 5". The comb webs 6 and 6' extend in the direction of the base web 11 of the grip arm 12, in each case starting from a side of the grip arm 12 facing away from the grip arm 14.

A directional abutment 9 of the bending joint 15, i.e. an abutment that is active only in the direction of pushing apart A of the two grip arms 12, 14, is in the present case formed by the mutually facing end faces 19, 19' of two adjacent comb webs 6, 6'. (This can be seen better in FIG. 3). Thus, when the two grip arms 12, 14 are pushed apart A, the end faces 19, 19' of two adjacent comb webs 6, 6' are pressed onto each other, whereby the directional abutment is active in the direction of pushing apart A of the two grip arms 12, 14.

To sum up, and as has been described with reference to FIG. 1, a bending joint 15 therefore has at least one slit 5, a base web 11, and a directional abutment 9.

Since the gripping instrument 1 shown in FIG. 1 is about to be closed by pushing the grip arms 12, 14 together, the directional abutment 9 is not active. Instead, by a bending of the bending joint 15, a limited force is transmitted via the grip arm 12 with the bending joint 15. It can also be clearly seen in FIG. 1 that the slits 5 and 5' closer to the pivot joint 3 are already spread slightly, whereas the slit 5" farther from the pivot joint 3 is still closed here. The bending joint 15 is therefore situated in a midways bending position, which permits further pushing together of the grip arms 12 and 14.

In order to avoid a plastic deformation and/or a fracture of the grip arms 12 and 14 during the pushing together, both grip arms 12, 14 have a safety abutment 16 at their proximal end. The safety abutment 16 limits a pushing together of the two grip arms 12 and 14 in such a way that the bending joint 15 is only elastically deformed. As can be seen from FIG. 1, the safety abutment 16 can protrude like a knob from one grip arm 12, 14 in the direction of the respective other one. However, it is likewise conceivable for the safety abutment 16 to be formed by a plane surface of the grip arms 12, 14.

Figure 2:
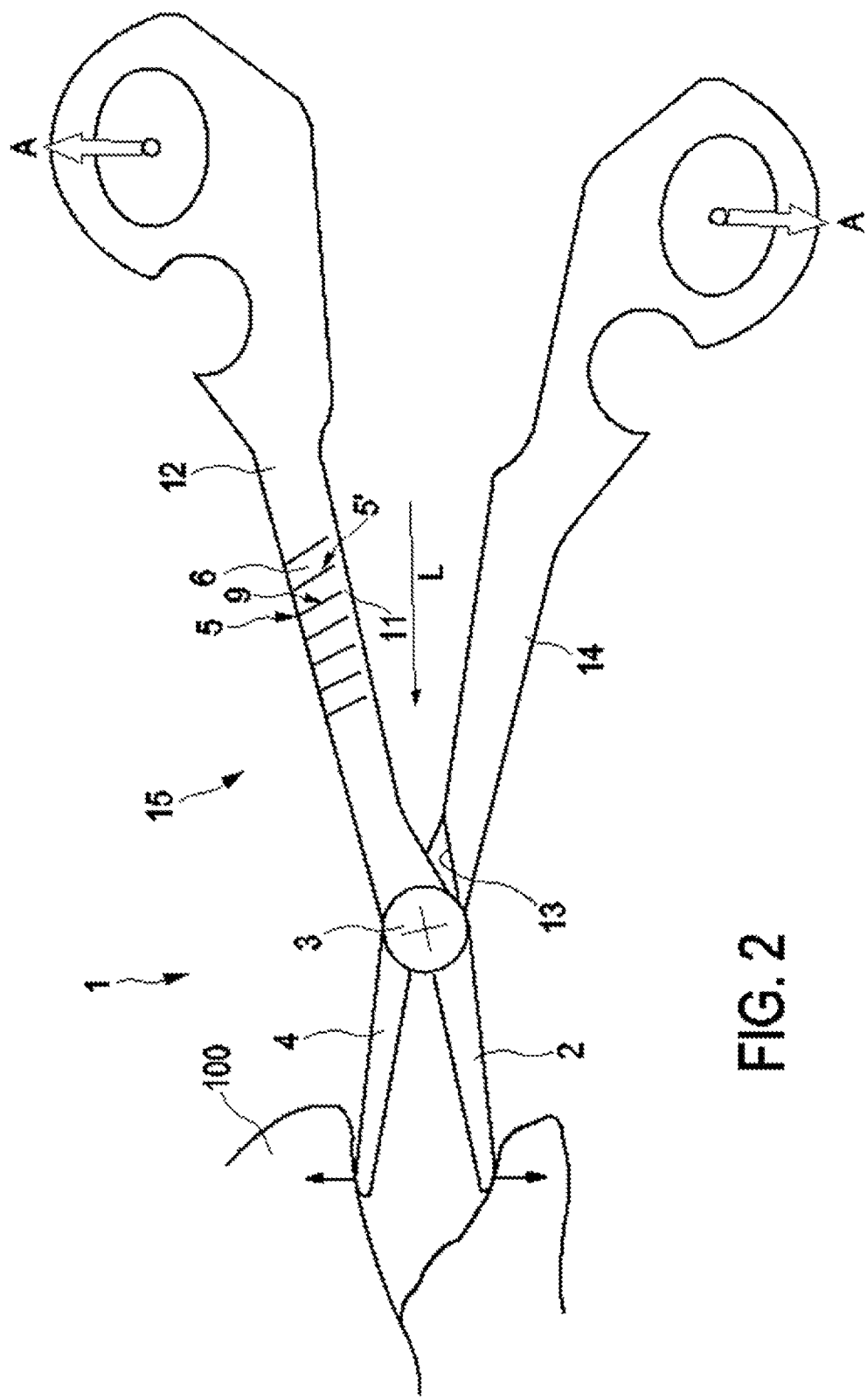
FIG. 2 shows the exemplary embodiment from FIG. 1 during the pushing apart of the grip parts.

In FIG. 2, the gripping instrument 1 from FIG. 1 is now shown during the pushing apart of the grip arms 12, 14 in direction A. In the situation shown, a biological tissue 100 is dissected. During the pushing apart A of the grip arms 12 and 14, the directional abutment 9 of the bending joint 15 is active. The end faces of the slits 5 and 5' and of the comb web 6 are pressed against each other, such that the entire manual force is transmitted via the grip arm 12 with the bending joint 15.

Figure 3:
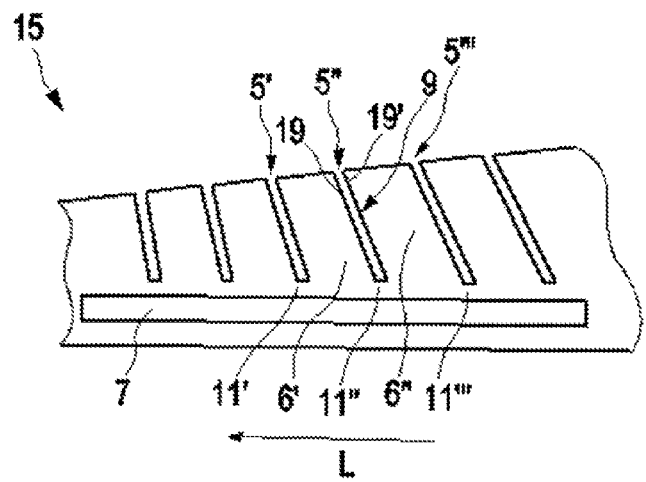
FIG. 3 shows a detail of a grip arm with bending element and spring element.

A variant of a bending joint 15 is now explained in detail with reference to FIG. 3. The bending joint 15 in FIG. 3 is shown in an unloaded state, i.e. the grip arms 12 and 14 (not shown here) are neither pushed together nor pushed apart. The bending joint 15 is formed by a base web 11, said base web 11 being free of the slits 5', 5" and 5'" of the grip arm.

Adjoining the slit 5", the end faces of the adjacent comb webs 6' and 6" are shown which in the present case form the directional abutment 9 of the bending joint 15. It can be clearly seen that each one of the slits arranged along a longitudinal direction L on the grip arm 12 has a directional abutment 9 of this kind. A spring element 7 is arranged along the base webs 11, 11' and 11" of the bending joint 15 and is completely embedded in the grip arm 12. The spring element 7 serves to stabilize the bending action of the bending joint 15 achieved through the base webs 11, 11' and 11" and can, for example, be composed of a strip of steel (spring steel), which is encapsulated by a plastic forming the rest of the grip arm.

Figure 4:
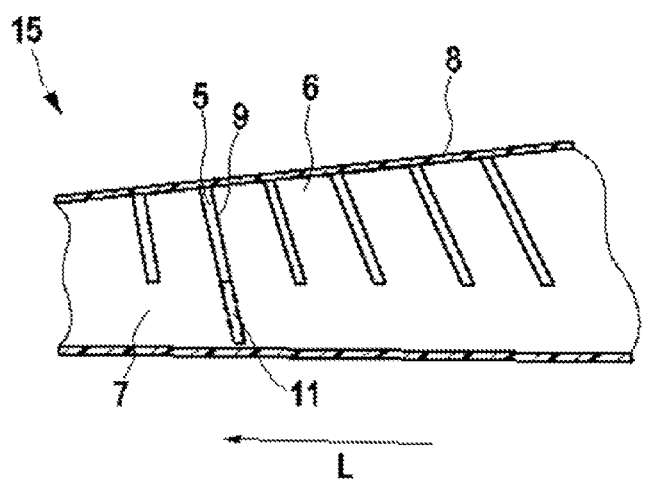
FIG. 4 shows a detail of a grip arm with a bending joint, which is enclosed by a sleeve.

According to another variant, depicted in FIG. 4, a bending joint 15 is enclosed by a flexible sleeve 8. The sleeve 8 in the present case is pushed on over the grip arm 12 and prevents entry of biological tissue and also of contaminants into the slit 5. The sleeve 8 is made so flexible that it does not tear during the pushing together of the grip arms. In other respects, the bending joint 15 in FIG. 4 corresponds to the one in FIG. 1 and FIG. 2. For clarity, a base web 11 is indicated by broken lines in FIG. 4.

Figure 5:
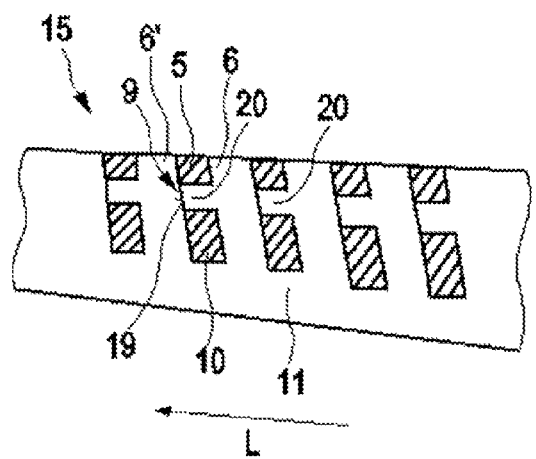
FIG. 5 shows a detail of another grip arm with a bending joint.

A third variant of a bending joint 15, depicted in FIG. 5, also has a slit 5 transverse to the longitudinal direction L of the grip arm 12. To achieve a desired bending action of the bending joint 15, this slit 5 is much wider in the longitudinal direction L than, for example, the slits described with reference to FIG. 3 and FIG. 4. However, in order to ensure an effective limiting of the force transmitted via the bending joint 15, the directional abutment 9 in the present case has a support element 20 protruding from the comb web 6 in the direction of an adjacent comb web 6'. Therefore, during the pushing apart of the two grip arms, the support element 20 only has to be pressed against the end face 19 in order to bring the directional abutment 9 into play, rather than the comparatively far apart end faces 19, 19' of two adjacent comb webs 6, 6' being pressed onto each other. The support element 20 thus braces the comb web 6 against the adjacent comb web 6' when the grip arms 12, 14 are moved away from each other. Accordingly, during the pushing apart of the grip arms 12 and 14 (not shown), an unlimited force is transmitted via the bending joint 15. It will also be seen clearly from FIG. 5 that the slit 5 is filled with a soft elastic filler component 10 (shown by hatching), which prevents entry of dirt or similar into the slit 5.

The slits 5, 5' and 5" in the exemplary embodiments described with reference to FIGS. 1 to 5 are spaced uniformly apart from one another in the longitudinal direction L of the grip arm 12. A uniform spacing relates to a bending joint in the unloaded state. Furthermore, the comb webs 6, 6', 6" in FIGS. 1 to 5 have an identical width. An identical width means a width of the comb webs in the foot area of the slits in the longitudinal direction L of the grip arm when the bending joint 15 is unloaded. Depending on the intended use, it is of course conceivable that the slits and/or the comb webs are spaced apart at different distances from one another and/or have different widths. Of course, a bending joint can be formed on just one of the grip arms or on both grip arms.

LIST OF REFERENCE SIGNS

1 gripping instrument
2, 4 jaw part
3 pivot joint
5, 5', 5" slit
6, 6', 6" comb web
7 spring element
8 sleeve
9 directional abutment
10 filler component
11, 11', 11" base web
12, 14 grip arm
13 rotation abutment
15 bending joint
16 safety abutment
19, 19' end faces
20 support element
100 biological tissue
A direction of pushing apart of the grip arms
L longitudinal direction of grip arm
Z direction of pushing together of the grip arms

The invention claimed is:

1. A gripping instrument comprising:
   two jaw parts connected to each other by a pivot joint;
   two grip arms connected to the two jaw parts, the two grip arms being movable towards each other by pushing together the two grip arms, and the two grips arms being movable away from each other by pushing apart of the grip arms; and
   a bending joint disposed in at least one grip arm of the two grip arms, wherein:
     the bending joint comprises:
       at least one slit made in one side of the at least one grip arm in which the bending joint is disposed and by a cross-sectional tapering of the at least one grip arm in which the bending joint is disposed; and
       a directional abutment formed by opposite end faces of the at least one slit;
     when the two grip arms are pushed together, a force limited by a resiliency of the bending joint is transmitted via the at least one grip arm in which the bending joint is disposed to a corresponding jaw part of the two jaw parts; and
     when the two grip arms are pushed apart, the opposite end faces of the at least one slit contact each other such that an applied manual force acts directly through the directional abutment.

2. The gripping instrument as claimed in claim 1, wherein the bending joint is formed in the at least one grip arm and integral with the at least one grip arm.

3. The gripping instrument as claimed in claim 1, wherein the at least one grip arm is slit on a side that faces away from the other grip arm.

4. The gripping instrument as claimed in claim 1, wherein the at least one slit is formed substantially transversely or obliquely with respect to the longitudinal direction of the grip arm.

5. The gripping instrument as claimed in claim 1, wherein the at least one slit is a plurality of slits, the plurality of slits being arranged along a longitudinal direction of the at least one grip arm, and the spacing between the plurality of slits defining a comb web.

6. The gripping instrument as claimed in claim 5, wherein the comb web has a support element protruding from it, the directional abutment including the support element, and the support element bracing the comb web against a respectively adjacent comb web when the grip arms are moved away from each other.

7. The gripping instrument as claimed in claim 5, wherein at least one of (i) the plurality of slits and (ii) the comb webs are spaced apart from each other at different distances.

8. The gripping instrument as claimed in claim 1, further comprising a spring element that is arranged along a base web of the bending joint.

9. The gripping instrument as claimed in claim 8, further comprising a spring element that is embedded in the at least one grip arm.

10. The gripping instrument as claimed in claim 1, wherein the at least one slit is filled with a soft elastic filler component.

11. The gripping instrument as claimed in claim 10, wherein the at least one slit is enclosed by a sleeve separate from the at least one grip arm.

12. The gripping instrument as claimed in claim 1, wherein the gripping instrument is a surgical gripping instrument.

13. The gripping instrument as claimed in claim 1, wherein the gripping instrument has a rotation abutment, which limits a movement of the jaw parts toward each other.

14. The gripping instrument as claimed in claim 1, wherein a jaw part of the two jaw parts and a corresponding grip arm connected to the jaw part are formed integrally.

15. The gripping instrument as claimed in claim 1, wherein the at least one slit is enclosed by a sleeve separate from the at least one grip arm.

16. The gripping instrument as claimed in claim 1, further comprising a spring element that is embedded in the at least one grip arm.

* * * * *